US 11,869,533 B2

(12) United States Patent
Grimm

(10) Patent No.: US 11,869,533 B2
(45) Date of Patent: Jan. 9, 2024

(54) METHOD AND APPARATUS FOR TIREDNESS DETECTION

(71) Applicant: Dr. Ing. h.c. F. Porsche Aktiengesellschaft, Stuttgart (DE)

(72) Inventor: Michael Grimm, Weissach (DE)

(73) Assignee: Dr. Ing. h. c. F. Porsche AG, Stuttgart (DE)

( * ) Notice: Subject to any disclaimer, the term of this patent is extended or adjusted under 35 U.S.C. 154(b) by 24 days.

(21) Appl. No.: 17/673,353

(22) Filed: Feb. 16, 2022

(65) Prior Publication Data

US 2022/0284918 A1 Sep. 8, 2022

(30) Foreign Application Priority Data

Mar. 5, 2021 (DE) .................... 10 2021 105 311.0

(51) Int. Cl.
*G10L 25/51* (2013.01)
*H04R 1/40* (2006.01)
*G10L 21/0208* (2013.01)
*H04R 3/00* (2006.01)

(52) U.S. Cl.
CPC .......... *G10L 25/51* (2013.01); *G10L 21/0208* (2013.01); *H04R 1/406* (2013.01); *H04R 3/005* (2013.01); *H04R 2499/13* (2013.01)

(58) Field of Classification Search
CPC ..... G10L 25/51; G10L 21/0208; H04R 1/406; H04R 3/005; H04R 2499/13
USPC ............................................ 381/56, 58, 122
See application file for complete search history.

(56) References Cited

U.S. PATENT DOCUMENTS

| 2011/0087079 | A1* | 4/2011 | Aarts .................... A61B 7/003 600/300 |
| 2016/0046298 | A1 | 2/2016 | DeRuyck et al. |
| 2018/0137837 | A1* | 5/2018 | Peana ................... H05B 47/00 |
| 2018/0144746 | A1* | 5/2018 | Mishra ................. G06V 40/172 |
| 2020/0074154 | A1 | 3/2020 | el Kaliouby et al. |
| 2020/0359954 | A1 | 11/2020 | Sunagawa et al. |
| 2021/0073561 | A1* | 3/2021 | Ben Abdelaziz ...... G06V 40/23 |
| 2021/0129748 | A1 | 5/2021 | Tamrakar et al. |

FOREIGN PATENT DOCUMENTS

| DE | 102014008791 | 12/2015 |
| DE | 102018204695 | 12/2018 |
| GB | 2573738 | 11/2019 |

OTHER PUBLICATIONS

GB Examination Report dated Aug. 31, 2022.

\* cited by examiner

*Primary Examiner* — William A Jerez Lora
(74) *Attorney, Agent, or Firm* — Gerald E. Hespos; Michael J. Porco

(57) ABSTRACT

A method and apparatus (100) are provided for detecting tiredness of a vehicle driver. The apparatus (100) is configured to receive a signal from at least one microphone (104), to acquire a time characteristic of yawning actions in the signal, and to use an analysis of the time characteristic to detect or not detect a tiredness of the driver (106) from a frequency of yawning, a yawn intensity and/or a temporal compression between successive yawning actions.

8 Claims, 2 Drawing Sheets

METHOD AND APPARATUS FOR TIREDNESS DETECTION

CROSS REFERENCE TO RELATED APPLICATION

This application claims priority under 35 USC 119 to German Patent Appl. No. 10 2021 105 331.0 filed on Mar. 5, 2021, the entire disclosure of which is incorporated herein by reference.

BACKGROUND

Field of the Invention

The invention is based on an apparatus and a method for tiredness detection, in particular for a driver of a vehicle.

Related Art

A tired driver can be detected by means of steering angle monitoring or a driver observation camera.

With steering angle monitoring, it is difficult to distinguish between tired and non-tired drivers. Driver observation cameras require an additional component and add to the complexity and cost of the vehicle.

GB 2 573 738 discloses a driver yawn detection system using microphones.

SUMMARY

The invention relates to an apparatus for tiredness detection. The apparatus is configured to receive a signal from at least one microphone, to acquire a time characteristic of yawning actions in the signal, and to use an analysis of the time characteristic to detect or not detect a tiredness of the driver from a frequency of yawning, a yawn intensity and/or a temporal compression between successive yawning actions. A microphone installed in a vehicle can be used to detect the yawning of the driver. A temporal analysis of this kind is used to infer the tiredness of the driver from the frequency of yawning, the yawn intensity and the temporal compression between successive yawning actions.

The apparatus of some embodiments is designed to evaluate the signal in the analysis using pattern recognition and/or artificial intelligence.

The at least one microphone or the apparatus can comprise at least one filter designed to filter the signal to eliminate sounds other than yawning sounds.

The apparatus can be designed to analyze signals by extracting paralinguistic traits, such as a pitch characteristic, a continuity of a tonal characteristic and/or at least one spectral trait. The apparatus may detect a chronological succession of audible inhalation and tonal exhalation in the time characteristic and to determine a result of the analysis on the basis of the chronological succession.

The apparatus may receive signals from different microphones and the signals may be filtered using filters. The apparatus then performs the analysis on the plural signals. Microphones in a vehicle may be focused on the driver by beamforming and are highly performant even with high levels of background noise. Assuming appropriate consent from the driver, the signals from the microphones can be analyzed at any time. The tiredness of the driver is therefore detected particularly reliably.

The invention also relates to a vehicle that has the apparatus and at least one microphone in an interior of the vehicle. The at least one microphone is designed to capture audible sound coming from a driver of the vehicle and to transmit a corresponding signal to the apparatus.

The invention also relates to a method for tiredness detection. The method includes receiving a signal from at least one microphone, acquiring a time characteristic of yawning actions in the signal, and analyzing the time characteristic to be used to detect or not detect a tiredness of the driver from a frequency of yawning, a yawn intensity and/or a temporal compression between successive yawning actions.

The signal may be evaluated in the analysis using pattern recognition and/or artificial intelligence.

The method may include filtering the signal using a filter to eliminate sounds other than yawning sounds.

The step of analyzing signal may include extracting paralinguistic traits, such as a pitch characteristic, a continuity of a tonal characteristic and/or at least one spectral trait. A chronological succession of audible inhalation and tonal exhalation may be detected in the time characteristic and a result of the analysis may be determined on the basis of the chronological succession.

DETAILED DESCRIPTION

Figure 1:
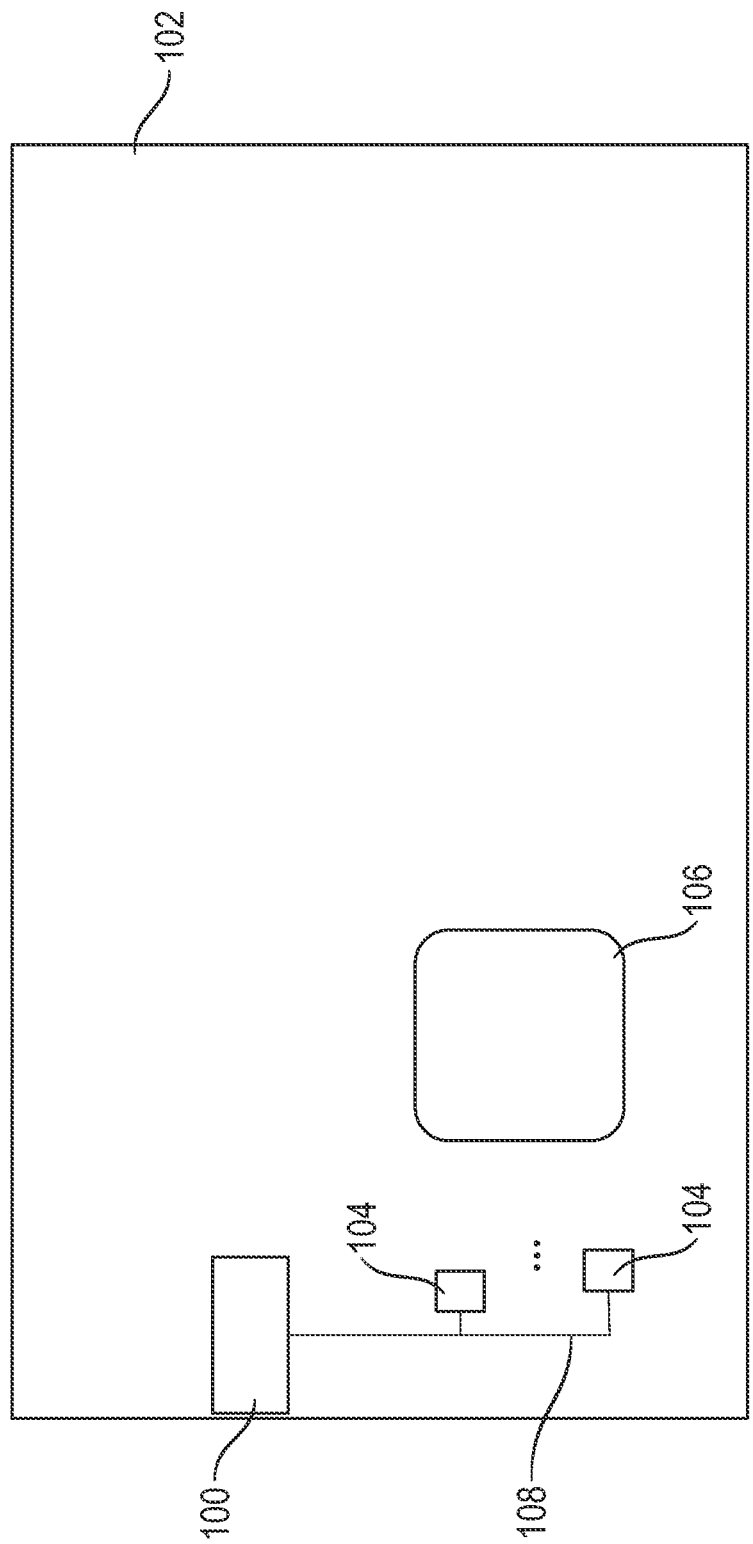
FIG. 1 schematically shows an apparatus for tiredness detection in a vehicle.

FIG. 1 schematically shows parts of an apparatus 100 for tiredness detection in a vehicle 102.

The vehicle 102 comprises the apparatus 100 and at least one microphone 104. The embodiment shown in FIG. 1 has plural microphones 104 arranged in an interior of the vehicle 102 and designed to capture audible sounds coming from a driver 106 of the vehicle 102 and to transmit a corresponding signal to the apparatus 100 via a signal line 108.

The apparatus 100 is configured to receive a signal from at least one of the microphones 104.

The apparatus 100 acquires a time characteristic of yawning actions in the signal. The apparatus 100 can comprise at least one filter designed to filter the signal to eliminate sounds other than yawning sounds. The apparatus 100 is configured to use an analysis of the time characteristic to detect or not detect a tiredness of the driver 106 from a frequency of yawning, a yawn intensity and/or a temporal compression between successive yawning actions. The apparatus 100 and the other elements shown in FIG. 1 and/or described herein may be implemented in various forms of hardware, software or combinations thereof. Preferably, these elements are implemented in a combination of hardware and software on one or more appropriately programmed general-purpose devices that may include a processor, memory and input/output interfaces. The term "connected" as used herein is defined to mean directly connected to or indirectly connected with through one or more intermediate components. Such intermediate components may include both hardware and software-based components.

It will be appreciated by those skilled in the art that the block diagrams presented herein represent conceptual views of illustrative circuitry embodying the principles of the disclosure. Similarly, any functions or methods implied by these block diagrams may be represented in computer readable media and so executed by a computer or processor, whether or not such computer or processor is explicitly shown.

The apparatus 100 evaluates the signal in the analysis using pattern recognition. For example, the apparatus 100 is designed to detect a chronological succession of audible inhalation and tonal exhalation in the time characteristic and to determine a result of the analysis on the basis of the chronological succession.

The apparatus 100 of FIG. 1 is designed to analyze the signal by extracting paralinguistic traits, in particular a pitch characteristic, a continuity of a tonal characteristic and/or at least one spectral trait.

Additionally or instead, the apparatus 100 can evaluate the signal in the analysis using artificial intelligence. The artificial intelligence in this case has previously been trained to detect tiredness from the described time characteristic.

The apparatus 100 can receive plural signals, that are filtered using filters, from different microphones 104 and performs the analysis using the plural signals.

Figure 2:
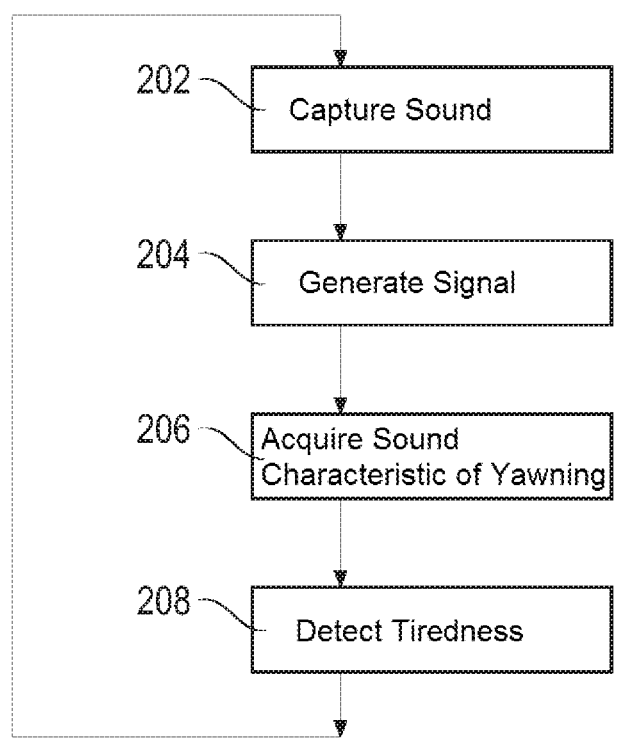
FIG. 2 shows steps in a method for tiredness detection.

Steps in a method for tiredness detection are described below with reference to FIG. 2. The method is carried out when the vehicle is used by a driver.

Step 202 includes capturing an audible sound by at least one of the microphones 104. There can be provision for the audible sound to be captured only if the driver 106 has signalled his agreement thereto.

Step 204 includes generating the signal corresponding to the audible sound. The signal can be filtered using the filter to eliminate sounds other than yawning sounds.

Step 206 includes acquiring a time characteristic of yawning actions in the signal. Steps 202 to 204 are performed repeatedly in the example and the time characteristic is recorded continuously.

Step 208 includes analyzing the time characteristic to detect or not detect a tiredness of the driver from a frequency of yawning, a yawn intensity and/or a temporal compression between successive yawning actions. Step 208 can be carried out in parallel with steps 202 to 206, in particular after the time characteristic for a predefined period was recorded. Step 208 also can be carried out after one of steps 202 to 206.

The signal is evaluated in the analysis using pattern recognition and/or artificial intelligence.

The signal can be analyzed by extracting paralinguistic traits.

The method further may include generating an audible, visible and/or tactile stimulus to warn the driver 106 if tiredness was detected and otherwise not to warn the driver 106. The audible stimulus can be an acoustic alarm. The visible stimulus can be lights on a dashboard or instrument panel. The tactile stimulus can be vibration of the steering wheel or seat.

In accordance with the invention, a pitch characteristic, a continuity of a tonal characteristic, and/or at least one spectral trait can be analyzed. A chronological succession of audible inhalation and tonal exhalation is detected in the time characteristic, and a result of the analysis is determined on the basis of the chronological succession.

What is claimed is:

1. An apparatus for tiredness detection, the apparatus being configured to receive a signal from at least one microphone, to acquire a time characteristic of yawning actions in the signal, and to use an analysis of the time characteristic to detect or not detect a tiredness of the driver from a frequency of yawning, a yawn intensity and/or a temporal compression between successive yawning actions, wherein the apparatus is designed to analyze the signal by extracting paralinguistic traits, in particular a pitch characteristic, a continuity of a tonal characteristic and/or at least one spectral trait, the apparatus being designed to detect a chronological succession of audible inhalation and tonal exhalation in the time characteristic and to determine a result of the analysis on the basis of the chronological succession.

2. The apparatus of claim 1, wherein the apparatus is designed to evaluate the signal in the analysis using pattern recognition and/or artificial intelligence.

3. The apparatus of claim 2, wherein the at least one microphone or the apparatus comprises at least one filter designed to filter the signal in to eliminate sounds other than yawning sounds.

4. The apparatus of claim 1, wherein the apparatus is designed to receive a plurality of signals from a plurality of microphones, the signals being filtered using filters associated with the respective microphones and the apparatus performing the analysis using the plurality of signals.

5. A vehicle comprising the apparatus of claim 1, wherein the at least one microphone is arranged in an interior of the vehicle and is designed to capture audible sound coming from a driver of the vehicle and to transmit a corresponding signal to the apparatus.

6. A method for tiredness detection, the method comprising: receiving a signal from at least one microphone, acquiring a time characteristic of yawning actions in the signal, analyzing the time characteristic to detect or not detect a tiredness of the driver from a frequency of yawning, a yawn intensity and/or a temporal compression between successive yawning actions, wherein the signal is analyzed by extracting at least one paralinguistic trait selected from the group consisting of a pitch characteristic, a continuity of a tonal characteristic, and/or at least one spectral trait, a chronological succession of audible inhalation and tonal exhalation being detected in the time characteristic and a result of the analysis being determined on the basis of the chronological succession.

7. The method as claimed in claim 6, wherein the signal is evaluated in the analysis using pattern recognition and/or artificial intelligence.

8. The method of claim 6, wherein the signal is filtered using a filter in order to eliminate sounds other than yawning sounds.

* * * * *